(12) United States Patent
Tan et al.

(10) Patent No.: US 11,833,207 B2
(45) Date of Patent: Dec. 5, 2023

(54) ADIPOCYTE-TARGETING DNA NANODRUG AND PREPARATION AND USES THEREOF

(71) Applicant: HUNAN UNIVERSITY, Hunan (CN)

(72) Inventors: Weihong Tan, Hunan (CN); Yanlan Liu, Hunan (CN); Lili Zhang, Hunan (CN)

(73) Assignee: HUNAN UNIVERSITY, Changsha (CN)

( * ) Notice: Subject to any disclaimer, the term of this patent is extended or adjusted under 35 U.S.C. 154(b) by 258 days.

(21) Appl. No.: 17/131,600

(22) Filed: Dec. 22, 2020

(65) Prior Publication Data

US 2021/0290768 A1 Sep. 23, 2021

(30) Foreign Application Priority Data

Mar. 18, 2020 (CN) .......................... 202010190961.9

(51) Int. Cl.
*A61K 47/54* (2017.01)
*A61K 31/7024* (2006.01)
*A61P 3/10* (2006.01)

(52) U.S. Cl.
CPC ........ *A61K 47/549* (2017.08); *A61K 31/7024* (2013.01); *A61P 3/10* (2018.01)

(58) Field of Classification Search
CPC ....... A61K 47/579; A61K 9/5176; A61P 3/04; A61P 3/10
See application file for complete search history.

(56) References Cited

FOREIGN PATENT DOCUMENTS

| CN | 108727471 A | 11/2018 |
| CN | 111068070 A | 4/2020 |
| CN | 111388452 A | 7/2020 |

OTHER PUBLICATIONS

Zhang et al. (Angew. Chem. Int. Ed., 2021, vol. 6):10745-10755, plus Supporting Information).*

* cited by examiner

*Primary Examiner* — Terra C Gibbs

(57) ABSTRACT

An adipocyte-targeting DNA nanodrug, and preparation and uses thereof. The drug is composed of an adipocyte-targeting DNA microstructure and tannic acid (TA) in a weight ratio of 1:25-30. Among them, the small molecular antioxidant TA is loaded into the DNA microstructure. The DNA microstructure incorporated with an adipocyte-targeting aptamer sequence can specifically recognize and bind with adipocytes. TA and DNA microstructure can interact with each other through multiple hydrogen bonds to form the adipocyte-targeting, safe and efficient DNA nanodrug.

9 Claims, 16 Drawing Sheets

Specification includes a Sequence Listing.

ADIPOCYTE-TARGETING DNA NANODRUG AND PREPARATION AND USES THEREOF

REFERENCE TO AN ELECTRONIC SEQUENCE LISTING

The contents of the electronic sequence listing (Sequence-Listing-20210203.txt; Size: 2,000 bytes; and Date of Creation: Feb. 3, 2021) is herein incorporated by reference in its entirety.

CROSS-REFERENCE TO RELATED APPLICATIONS

This application claims the benefit of priority from Chinese Patent Application No. 202010190961.9, filed on Mar. 18, 2020. The content of the aforementioned application, including any intervening amendments thereto, is incorporated herein by reference in its entirety.

TECHNICAL FIELD

This application relates to nanodrugs, and more particularly to an adipocyte-targeting DNA nanodrug, and preparation and uses thereof.

BACKGROUND

Obesity is a multifactorial, chronic metabolic disease correlated with an increased risk of numerous conditions including diabetes, hypertension, non-alcoholic fatty liver, cancer, and both cardiovascular and neurological diseases. It is nowadays considered the most serious public health disease worldwide. Currently, many clinical and preclinical pharmaceutical attempts have been made to control and prevent obesity from progressing to other disorders by manipulating the body's energy intake, absorption or metabolism, but they generally struggle with limited and variable efficacy in different patients and come with harsh side effects, eventually leading to treatment failure or even life-threatening consequences. Given the above, it is of great significance to develop a safe, effective and widely applicable treatment option for obesity and its related complications in order to improve the quality of life for patients and reduce the risk of major complications.

SUMMARY

An object of this application is to provide an adipocyte-targeting DNA nanodrug, and a preparation and application thereof, where the nanodrug is safe, stable and adjustable in size, while also having significant antioxidant and anti-inflammatory effects.

Technical solutions of this application are specifically described as follows.

In the first aspect, this application provides an adipocyte-targeting DNA nanodrug, comprising:

an adipocyte-targeting DNA microstructure (TDM) and tannic acid;

wherein TDM has a densely layered structure; the tannic acid is loaded into the TDM by way of multiple hydrogen bonds to fabricate the adipocyte-targeting DNA nanodrug; and a weight ratio of the adipocyte-targeting DNA microstructure TDM to the tannic acid is 1:25-30.

In an embodiment, the adipocyte-targeting DNA microstructure TDM has an average size of 1-2 μm.

In an embodiment, the adipocyte-targeting DNA microstructure TDM is formed from a DNA sequence as shown in SEQ ID NO: 1 through a rolling circle replication and DNA self-assembly technology.

In a second aspect, this application provides a method of preparing the adipocyte-targeting DNA microstructure TDM, comprising:

(1) Ligation mixing a phosphorylated DNA template (SEQ ID NO: 1) designed with an adipocyte-specific aptamer sequence and a primer (SEQ ID NO: 2) in a DNA ligase buffer; annealing the reaction mixture; and subjecting the annealed product to ligation in the presence of *E. coli* DNA ligase to form a circularized DNA; and (2) Polymerization subjecting the circularized DNA template to polymerization in a polymerase buffer containing bovine serum albumin (BSA) in the presence of dNTP and phi29 DNA polymerase; heating the reaction mixture to terminate the polymerization to obtain a final product; and washing the final product to obtain the adipocyte-targeting DNA microstructure TDM.

In an embodiment, in step (1), a concentration of the phosphorylated DNA template is 8-12 μM; a concentration of the primer is 8-12 μM; the DNA ligase buffer contains 5 mM of Tris-HCl, 1 mM of $MgCl_2$, 0.1 mM of ATP and 1 mM of dithiothreitol; a concentration of the *E. coli* DNA ligase is 50-70 U/μL; a volume ratio of the phosphorylated DNA template to the primer to the DNA ligase buffer to the *E. coli* DNA ligase is (2-4):(5-7):(30-60):(7-9); the annealing is programmed as follows: 95° C. for 5 min and cool to room temperature within 2 h; and the ligation is performed at 16° C. for 3 h.

In an embodiment, in step (2), a concentration of the circularized DNA template is 0.5-0.7 μM; a concentration of the phi29 DNA polymerase is 8-12 U/μL; a content of BSA is 0.04%-0.06%; the polymerase buffer contains 50 mM of Tris-HCl, 10 mM of $(NH_4)_2SO_4$, 10 mM of $MgCl_2$ and 4 mM of dithiothreitol in a volume ratio of (45-55):(15-25):(0.5-1.5):(95-105); the polymerization is performed at 28-32° C. for 18-30 h; and the heating is performed at 70-80° C. for 8-12 min.

In a third aspect, this application further provides a method for preparing the adipocyte-targeting DNA nanodrug (TADN), comprising:

adding a tannic acid (TA) solution to a solution of the TDM to obtain a mixture;

continuously mixing the mixture at a preset temperature under shaking followed by centrifugation to collect the adipocyte-targeting DNA nanodrug TADN.

In an embodiment, the concentration of the solution of the TDM is 0.2-0.4 μM; the concentration of the TA solution is 5-15 mM; and the volume ratio of the solution of the TDM to the TA solution is (0.5-1.5):(0.5-1.5).

In a fourth aspect, this application also provides a method for treating obesity in a subject in need thereof, comprising:

administering a therapeutically effective amount of the adipocyte-targeting DNA nanodrug to the subject.

The design principle of the invention is described as follows. Unlike conventional, complicated Watson-Crick base pairing-dependent DNA sequence design methods, we develop a template-assisted strategy for successful manufacturing of multifunctional DNA structures TDM, in combination with rolling circle replication (RCR) and dense packaging-driven DNA self-assembly processes. Then, the hierarchical structure of TDM is engineered by phenolic groups of TA, mainly through multiple hydrogen bonds, which enable high loading of TA within DNA frameworks to form the adipocyte-targeting DNA nanodrug TADN. Meanwhile, TA could compress the assembled DNA structure, endowing TADN with size-controllable and surface-controllable properties. Given the above, the multifunctional TADN formed through the strong hydrogen bond interaction presents not only controllable sizes, high TA loading capacity and excellent antioxidant and anti-inflammatory activities, but also the adipocytes-binding ability. Upon specifically entering into adipocytes, the TADN can broadly and efficiently scavenge multiple reactive oxygen and nitrogen species (RONS) to lower the intracellular RONS level, blocking the intracellular inflammatory pathways and the signal communication between adipocytes and macrophages. As a consequence, the accumulation of lipid droplets is greatly alleviated in adipocytes, providing a specific antiobesity effect.

Compared to the prior art, this application has the following beneficial effects.

(1) The DNA nanodrug of the disclosure includes a DNA microstructure TDM and tannic acid (TA) loaded thereon. The TDM incorporated with an adipocyte-targeting aptamer sequence and the housed tannic acid within DNA scaffold are permitted to form the adipocyte-targeting DNA nanodrug for effectively targeting and specifically entering into adipocytes. Moreover, since the tannic acid has excellent antioxidant and anti-inflammatory activities, the adipocyte-targeting nanodrugs efficiently suppress adipose differentiation and the overactivation of innate immune cells via improving redox dyshomeostasis and chronic inflammation environment in adipose tissues, thus maximizing the antiobesity effect and minimizing interference with normal metabolism.

(2) The DNA nanodrug is composed of biomolecular nucleotides and TA, contributing to its good biocompatibility. Moreover, the DNA nanodrug is designed according to the microenvironment (oxidative stress and chronic excessive inflammation) shared by the obesity and related complications, which enables a desirable therapeutic effect. The safe and adipocyte-targeting nanodrugs with antioxidative and anti-inflammatory properties can smartly balance the therapeutic efficacy and safety of anti-obesity therapy.

(3) The TDM has a high loading capacity for TA due to the presence of a large number of TA binding sites thereon. Moreover, TA also exhibits the ability to compress the TDM, endowing the DNA microstructure with size-controllable and morphology-controllable properties.

DETAILED DESCRIPTION OF EMBODIMENTS

Figure 1:
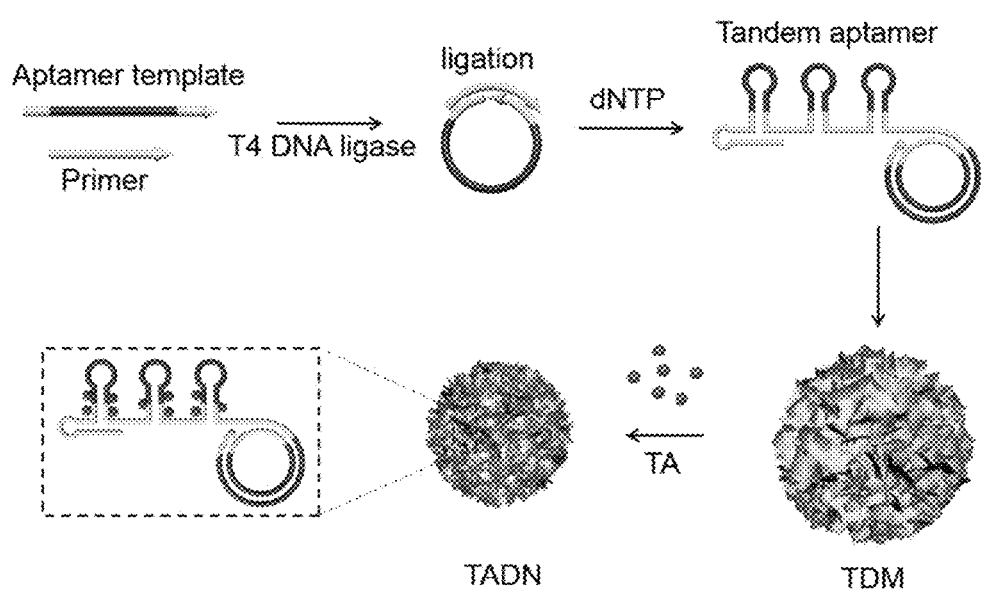
FIG. 1 schematically depicts the synthesis process of an adipocyte-targeting DNA nanodrug according to an embodiment of the disclosure.

Example 1 Preparation of an adipocyte-targeting DNA nanodrug

The preparation of the adipocyte-targeting DNA nanodrug of the disclosure was schematically shown in FIG. 1, and was specifically prepared as follows.

(1) Ligation

A phosphorylated DNA template (10 μM, 0.6 μL) (as shown in SEQ ID NO: 1) incorporated with an adipocyte-targeting aptamer sequence (MA-91) and a primer (10 μM, 1.2 (SEQ ID NO: 2) were mixed in 10 μL of a DNA ligase buffer containing 5 mM of Tris-HCl, 1 mM of $MgCl_2$, 0.1 mM of ATP and 1 mM of dithiothreitol. Then the reaction mixture was annealed by heating at 95° C. for 5 min and then showly cooling to room temperature within 2 h. The annealed product was subjected to ligation in the presence of *E. coli* DNA ligase (60 U/μL, 1.6 μL) at 16° C. for 3 h to form a circularized DNA template.

(2) Polymerization

The circularized DNA template (0.6 μM, 5 phi29 DNA polymerase (10 U/μL, 2 μL), dNTP (10 mM/μL, 2 μL) and BSA (0.05%, 0.1 μL) were added to 10 μL of a polymerase buffer containing 50 mM of Tris-HCl, 10 mM of $(NH_4)_2SO_4$, 10 mM of $MgCl_2$ and 4 mM of dithiothreitol. The reaction mixture was heated at 30° C. for 24 h to allow the polymerization of the circularized DNA template, and then heated at 75° C. for 10 min to terminate the polymerization. To the end, the reaction product was washed twice with double distilled water to obtain an adipocyte-targeting DNA microstructure TDM, which was stored at −20° C. for use.

Figure 2A:
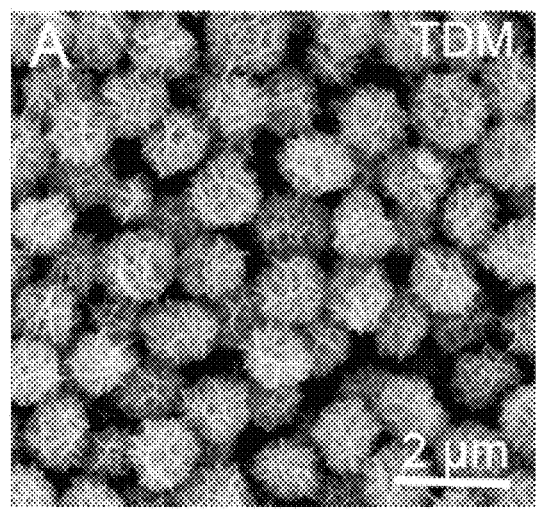
FIGS. 2A-B are scanning electron microscope (SEM) images of TDM and TADN prepared in Example 1, respectively.

The adipocyte-targeting DNA microstructure TDM carried the adipocyte-targeting aptamer sequence shown in SEQ ID NO: 1, and its stacked structure and microstructure were shown in FIGS. 1 and 2A.

(3) TA Loading into TDM

20 μL of a 0.3 μM TDM solution was mixed with tannic acid (10 mM, 20 μL) at 4° C. under shaking for 24 h, and then the reaction mixture was centrifuged. The precipitate was collected as the adipocyte-targeting DNA nanodrug TADN, and the absorbance of the supernatant was measured at 275 nm using a UV spectrophotometer (UV-2450, Shimadzu) to quantify the loading capacity of TA on TDM.

In the preparation of TADN, a weight ratio of the TDM to TA was 1:28.

Information of the sequences mentioned herein was presented in Table 1.

TABLE 1

Sequence Information

DNA

| | |
|---|---|
| SEQ ID NO: 1 | $PO_4^{3-}$-ATC GAC CTC TGG GTT ATG*CCT GCA GTG TGT GTG ATG* CCT GTT ATT TGG CCT GCC GGT GGG CCC AGC ACG CTT CCG CGC GTA CCA ACA ATT GTT GGT ACG |
| SEQ ID NO: 4 | $PO_4^{3-}$-ATC GAC CTC TGG GTT ATG*NNN NNN NNNNNNNNNNNNNNNNNNNNNNNNNNNNNNNN N*GGC CCA GCA CGC TTCCG CGC GTA CCA ACA ATT GTT GGT ACG |
| SEQ ID NO: 2 | CAT AAC CCA GAG GTC GAT CGT ACC AAC AAT TGT TGG |
| SEQ ID NO: 3 | CAC CGG CAG GCC AAA TAA CAG GCA TCA CAC ACA CTG CAG G |

Notes:
The sequence in bold was complementary to the primer DNA; the sequence in italics was complementary to the aptamer or a random control strand.

Notes: The sequence in bold was complementary to the primer DNA; the sequence in italics was complementary to the aptamer or a random control strand.

Figure 2B:
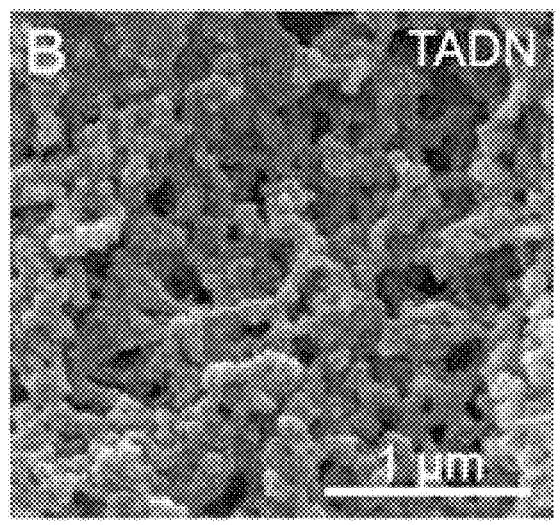
Figure 3:
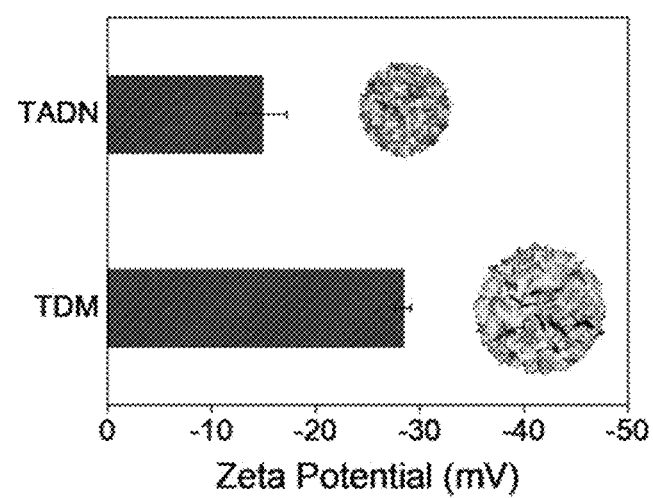
FIG. 3 shows Zeta potentials of TDM and TADN prepared in Example 1.
Figure 4:
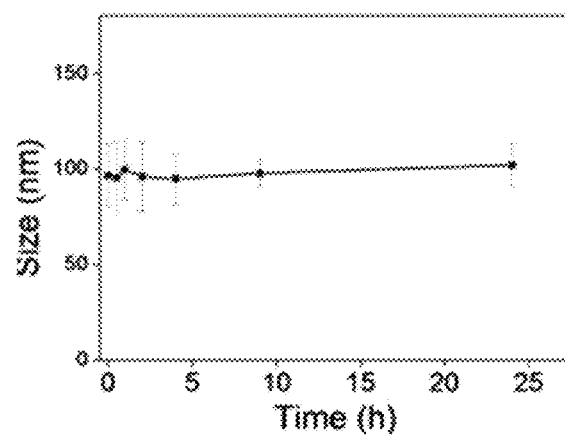
FIG. 4 illustrates the dynamic light scattering (DLS) analysis of TADN in PBS.
Figure 5:
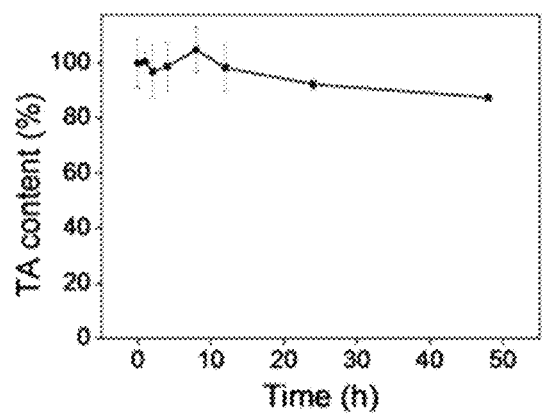
FIG. 5 shows the release profile of TA from TADN in PBS.
Figure 6:
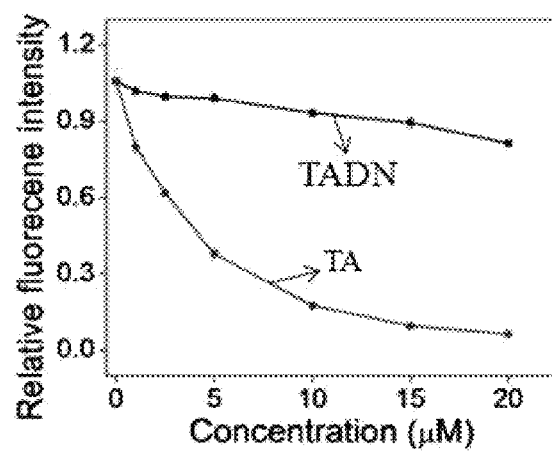
FIG. 6 shows nonspecific protein (BSA) absorption of TADN or free TA by monitoring the fluorescence of BSA.

As shown in FIG. 1, the TDM was firstly synthesized, and then applied to the construction of TADN. In the synthesis of TDM, an adipocyte-specific aptamer sequence was designed in the DNA template to construct the dense-layered scaffold TDM (as shown in FIG. 2A). The TDM provided herein not only produced monodisperse and size-controlled DNA structures with robust resistance to nuclease degradation, denaturation, or dissociation under harsh conditions, but also offered a versatile platform for built-in multifunctional moieties. To this end, adipocyte-targeting antioxidative DNA nanodrugs (TADN) were engineered by encoding an adipocyte-targeting aptamer sequence during RCR, followed by incorporation of tannic acid (TA), a natural small molecule with diverse biological functions including anti-oxidation and anti-inflammation (FIG. 2B). Interestingly, TA could compress the assembled DNA structure from the micrometer scale into a nanometer size as the loading time increased, coupled with morphological change from a hierarchical structure (about 1 μm) to spherical shape (about 100 nm), as characterized by scanning electron microscopy (SEM) imaging (FIGS. 2A-B). Meanwhile, the Z-potential became more negative (FIG. 3), which was attributable to large amounts of phenolic groups in TA. The TA loading capacity was determined to be 96% by weight, as measured by ultraviolet absorption spectrophotometer. Moreover, the resulting TADN could maintain its stability and cohesion under physiological conditions without obvious aggregation or release of TA from TADN (FIGS. 4-5). It was also worth noting that free TA molecules tended to absorb proteins which would lead to rapid and significant decrease of bioactivity. Impressively, we found that DNA nanostructures could efficiently protect TA molecules from protein adsorption (FIG. 6). Collectively, these results clearly indicated the potential use of TADN for in vivo applications.

Comparative Example 1

A control DNA microstructure NTDM was prepared according to the process and parameters in Example 1, and the difference was merely that the phosphorylated DNA template (SEQ ID NO: 1) incorporated with the adipocyte-targeting aptamer sequence (MA-91) was replaced with a random sequence, that was, N was input when the sequence was constructed. The NTDM had a sequence as shown in SEQ ID NO: 4, where N indicated a random nucleotide. The NTDM was further combined with TA to produce a DNA nanodrug NTADN.

Example 2 Investigation of Biological Activities of TADN

1. Scavenging Activity of TADN Against Reactive Oxygen and Nitrogen Species (RONS)

With the continuous adsorption of nutrients, various RONS were continuously produced and over accumulated in the body, which will raise the body's oxidative stress, and further induce related metabolic inflammation, insulin resistance and other complications. Therefore, the elimination of RONS may be an innovative, universal, safe and effective strategy in the intervention of obesity, and an antioxidant drug capable of eliminating various types of RONS was desired. However, traditional antioxidants struggled with narrow antioxidant activity, and thus struggled in the treatment of diseases. Given the above, a safe, specific, strong antioxidant was expected to scavenge a series of RONS, and as a promising antioxidant drug, TADN's antioxidant activity was deeply investigated herein.

(1) Investigation on the Scavenging Activity of TADN Against Superoxide Radicals ($O_2^{\cdot-}$) and Hydroxyl Radicals (·OH)

Electron paramagnetic resonance (EPR) measurements were performed to evaluate the $O_2^{\cdot-}$- and ·OH-scavenging abilities of DNA hybrid nanostructures TADN. DEPMPO was used as the trapper. $O_2^{\cdot-}$ was generated by dissolving $KO_2$ in DMSO/crown ether (0.2 M). ·OH was produced by the Fenton-type reaction using $H_2O_2$ and $CuSO_4$.

(2) Investigation on Scavenging Activity of TADN Against ·NO

The scavenging ability of TADN towards ·NO was carried out by EPR with carboxy-PTIO (Sigma Aldrich) as the trapper. NOC7 was used as the source of ·NO. For the EPR assay, carboxy-PTIO was dissolved in phosphate buffer (250 mM, pH 7.4), and NOC7 was dissolved in NaOH (1 mM). In a test tube, 0.5% methylcellulose was mixed with NOC7 (5 μM) for 30 min at room temperature, and the reaction mixture was then added into the carboxy-PTIO solution (5 μM) in the absence or presence of the DNA hybrid nanostructures.

(3) Investigation on Scavenging Activity of TADN Against ONOO$^-$

The ONOO$^-$ was prepared as follows. Briefly, 4 g of sodium nitrite were dissolved in 12 mL of water, and then added into 7.5 mL of 30% hydrogen peroxide. The resulting mixture was acidified with 2 mL of 96% sulfuric acid, followed by the rapid addition of 250 mL of a sodium hydroxide (12.5 g) aqueous solution. Excess hydrogen peroxide was removed by manganese dioxide for 15 min. The absorbance of the solution at 302 nm was measured to determine the concentration of ONOO$^-$. To study the scavenging ability of TADN towards ONOO$^-$, an ONOO$^-$ fluorescence probe synthesized by our group was received as a gift. Different concentrations of TADN were mixed with ONOO$^-$ (13.5 followed by incubation with ONOO$^-$ fluorescence probe (5 μM) for 1 h. The probe's fluorescence spectrum was recorded under excitation at 540 nm. ONOO$^-$ in each sample was quantified by comparing the fluorescent enhancement of the probe with the background or control samples.

(4) Investigation of Scavenging Activity of TADN Against Singlet Oxygen $^1O_2$ and Hydrogen Peroxide $H_2O_2$ The $^1O_2$ was derived from ChlorinE6 (Ce6), and singlet oxygen sensor green (SOSG) was used as an indicator for $^1O_2$. To study the $^1O_2$ scavenging ability of TADN, Ce6 (1 μM) and TADN were mixed with SOSG (2 μM) in PBS. The solution was then irradiated at an excitation wavelength of 404 nm for 5 min. The fluorescence of SOSG was then measured under excitation at 494 nm. $^1O_2$ in each sample was quantified by comparing the SOSG fluorescence enhancement with the background or control samples.

For $H_2O_2$-scavenging studies, a $H_2O_2$ fluorescence probe synthesized by our group was received as a gift. To study the $H_2O_2$ scavenging ability of TADN, the probe (20 μM) was mixed with TADN and $H_2O_2$ (150 μM) for 2 h. Then fluorescence spectra were recorded at the excitation wavelength of 420 nm.

Figure 7A:
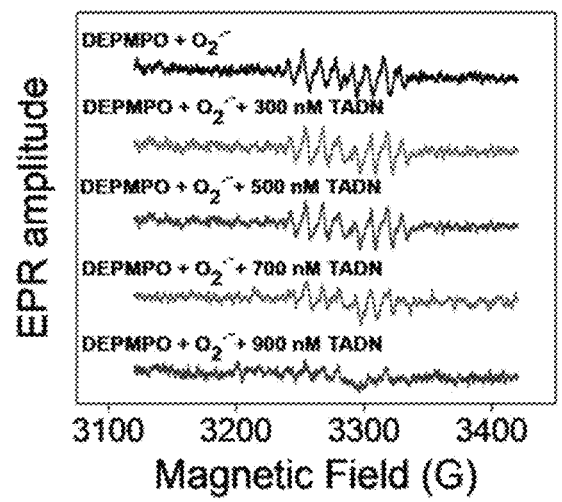
FIG. 7A shows the scavenging investigation of TADN against $O_2 \cdot^-$.
Figure 7B:
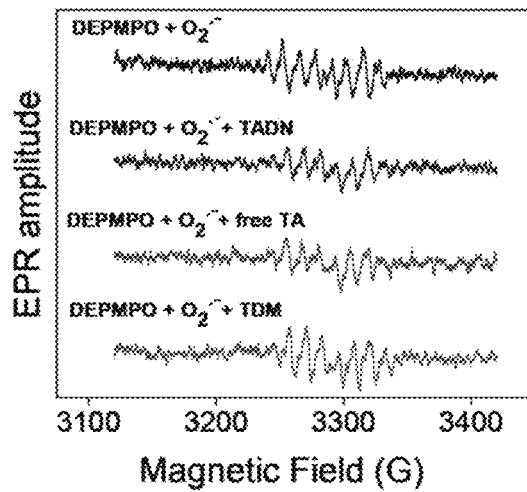
FIG. 7B illustrates the EPR measurements of the scavenging efficacy of TADN, TDM and TA towards $O_2 \cdot^-$.
Figure 8A:
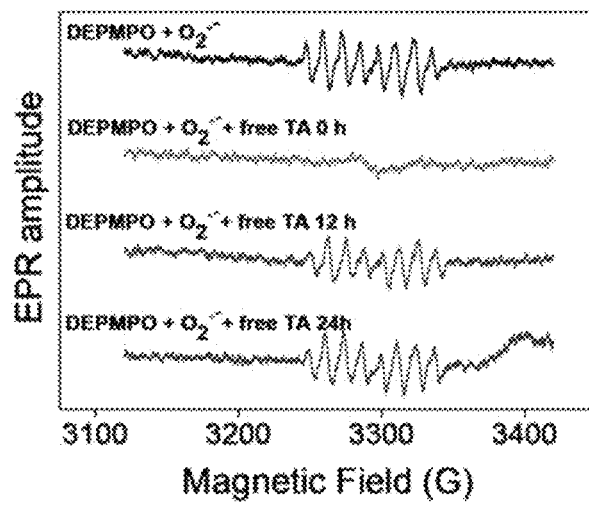
FIGS. 8A-B illustrate the EPR measurements of the $O_2 \cdot^-$-scavenging stability of free TA and TADN, respectively.
Figure 8B:
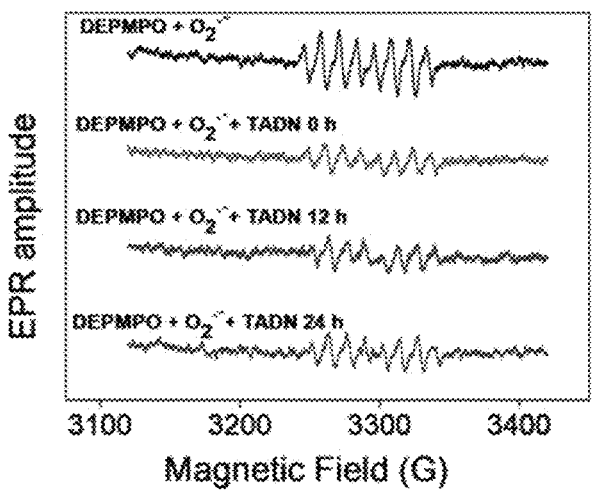
Figure 9:
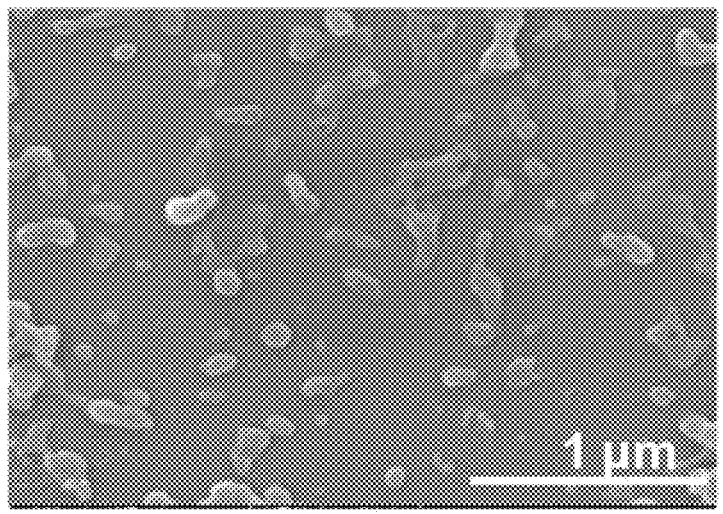
FIG. 9 is an SEM image of TADN upon reaction with $O_2 \cdot^-$.
Figure 10A:
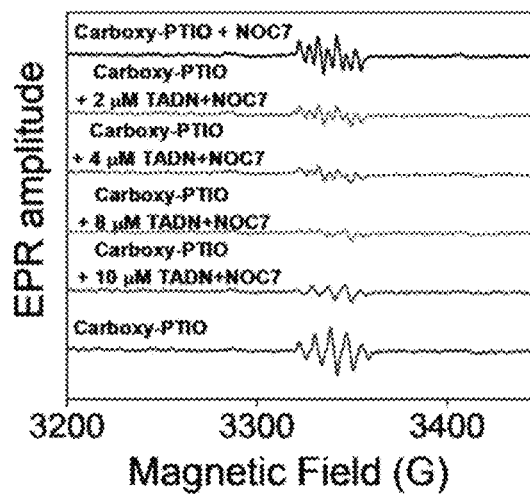
FIGS. 10A-E show scavenging investigation of TADN against various RONS, where 10A: $\cdot NO$; 10B: $\cdot OH$; 10C: $H_2O_2$; 10D: $^1O_2$; and 10E: $ONOO^-$; the scavenging effects of TADN against $O_2 \cdot^-$, $\cdot NO$ and $\cdot OH$ are measured by electron paramagnetic resonance (EPR) spectroscopy; and the scavenging capacities of TADN against $H_2O_2$, $^1O_2$ and $ONOO^-$ are measured by fluorescence spectroscopy.
Figure 10B:
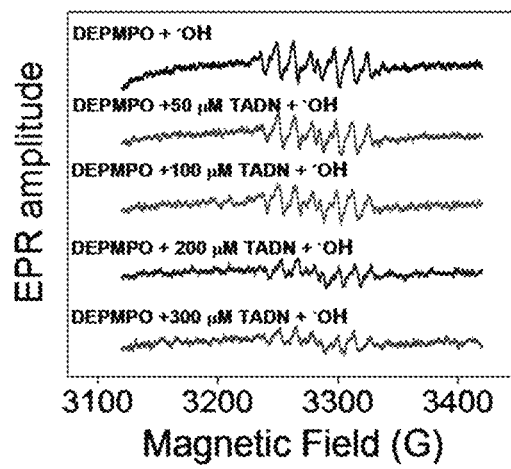
Figure 10C:
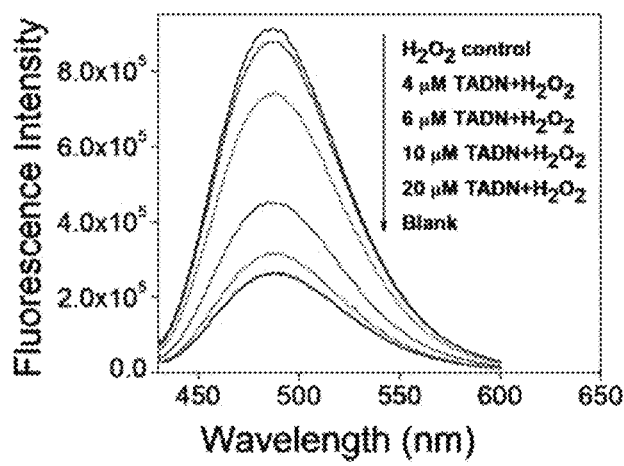
Figure 10D:
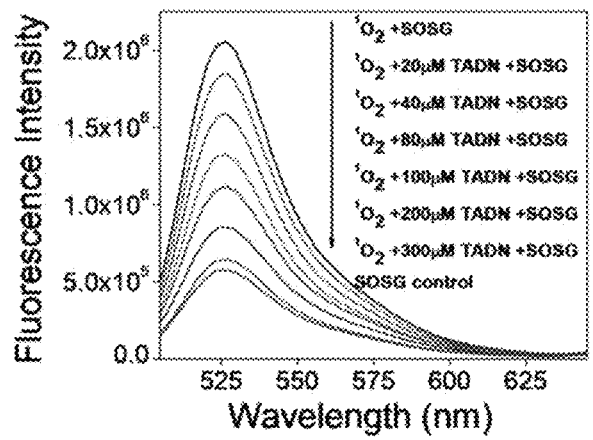
Figure 10E:
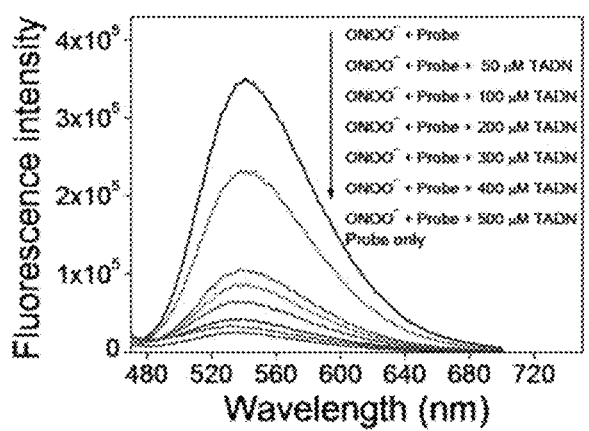

The analysis results of the scavenging activity of TADN against $O_2^{·-}$ were presented in FIG. 7A. In the absence of TADN, $O_2^{·-}$ reacted with DEPMPO to form DEPMPO-OOH with stable EPR amplitude. After the TADN was added, the signal intensity of DMPMPO-OOH began to decrease in a dose-dependent manner, and the EPR signal of DMPMPO-OOH gradually decreased to the background signal of DMPMPO at a concentration of 900 nM. Moreover, we also compared the antioxidative capability of TA-free TDM and free TA molecules. As shown in FIG. 7B, TDM demonstrated a weak $O_2^{·-}$-scavenging activity due to DNA's own antioxidant capacity. Though TA had a comparable scavenging activity to TADN, poor scavenging stability was noticed, and its $O_2^{·-}$-scavenging effect almost disappeared after 24 h as a consequence of vulnerable molecular structure (FIG. 8A), which further demonstrated why polyphenols failed to provide a desired therapeutic effect. Fortunately, those samples treated with TADN did not show obvious enhancement in the DEMPMPO-OOH signal, confirming that the TA in the TADN can maintain its antioxidant activity for a long time (FIG. 8B). Furthermore, TADN can maintain a complete spherical structure even in the presence of $O_2^{·-}$ (FIG. 9), which indicated that the maintenance of TA activity in TADN may be attributed to the protection effect of the DNA framework with high stability.

The analysis results of the scavenging activity of TADN against ·NO were presented in FIG. 10. As main RNS overproduced in different cells, nitroxide radicals (NO) participated in many physiological and pathophysiological processes. Particularly in the obesity-related diseases, the continuous production and accumulation of ·NO will induce oxidative damage, metabolic inflammation, steatosis, insulin resistance and other complications, and further promote weight gain. Thus, the scavenging effect of TADN against ·NO was explored using carboxy-PTIO and NOC-7 as the trapper and donor of ·NO, respectively. As shown in FIG. 10, carboxy-PTIO can be oxidized by ·NO from 5 lines (carboxy-PTIO) to 7 lines (carboxy-PTI). With the continuous removal of ·NO, the EPR signal will exhibit a spectral change from five-line hyperfine splitting to seven lines (FIG. 10).

In addition to direct oxidative damage, these two kinds of primary RONS (the superoxide and nitroxide free radicals) can also interact with each other or interact with other biological molecules to produce various secondary RONS to aggravate oxidative stress. However, there was no natural enzyme specific to these secondary RONS, and the existing antioxidants can hardly exhibit high efficiency in scavenging both primary and secondary RONS. In view of this, the scavenging activity of TADN against obesity-related secondary RONS, including ·OH, $H_2O_2$, $^1O_2$ and ONOO$^-$, was further investigated. Like the elimination of $O_2^{·-}$ and ·NO, the TADN can also down-regulate the content of these secondary RONS in a dose-dependent manner (FIG. 10).

The above results all demonstrated that the TADN had a wide range of scavenging ability against RONS and was expected to be effective in the treatment of obesity and obesity-related complications.

2. Cellular Test (1) Cytotoxicity Test

3T3-L1 preadipocytes were seeded in a 96-well plate at $10^4$/well. After culturing for 24 h, the preadipocytes were added with TA, TDM or TADN for another 24 h culture. The culture medium was removed, and the cells were washed twice with PBS, followed by the addition of 100 μL of fresh culture medium and 10 μL of CCK-8 for the CCK-8 assay according to the manufacturer's protocol. The UV absorbance of each well at 450 nm was recorded using a Synergy 2 multifunctional microplate reader (Bio-Tek, Winooski, Vt.).

(2) Obese Cell Model

The obese cell model was established as follows. Specifically, the 3T3-L1 preadipocytes were cultured in a DMEM medium containing 10% of FBS and 1% of penicillin-streptomycin at 37° C. and 5% $CO_2$. In order to induce the differentiation of 3T3-L1 preadipocytes, the DMEM complete medium was replaced with a differentiation medium (DMEM containing 10% of FBS, 1 μmol/L of dexamethasone, 0.5 mmol/L of 3-isobutyl-1-methylxanthine and 1.67 mol/L of insulin) for induction for 2 days. Then an adipocyte maintenance medium (DMEM containing 10% of FBS and 10 μg/mL of insulin) was cultured for a specific amount of time. The adipocyte maintenance medium was replaced every two days. Cell differentiation and the intracellular ROS change throughout the induction process were characterized by Oil Red 0 and $H_2$DCFDA, respectively.

(3) Test of Specific Recognition

The binding ability of TADN to adipocytes was investigated as follows. Specifically, 3T3-L1 preadipocytes and mature adipocytes were added into Cy5-TADN or Cy5-NTADN for 7 min in a binding buffer (containing 1 mL of 4.5 g/L of glucose, 5 mM of $MgCl_2$, 0.1 mg/mL of salmon sperm DNA (Sigma Aldrich, St. Louis, Mo.) and 10% of FBS). Then the cells were washed three times with a washing buffer (1 mL, 4.5 g/L glucose and 5 mM $MgCl_2$ in Dulbecco's Phosphate-Buffered Saline (D-PBS)). Thereafter, cells were suspended with 1 mL of the washing buffer and subjected to confocal imaging by using a FV1000-X81 confocal microscope (Olympus, Japan).

(4) Antiobesity Effect of TADN

For the antiobesity study, 3T3-L1 preadipocytes were differentiated into mature adipocytes using the above-mentioned method, followed by treatment with TADN, NTADN or TA once every three days. Then the treated cells were fixed with 4% paraformaldehyde for 10-20 min and stained with a 0.6% (w/v) oil red 0 solution. The stained cells were washed 3 times with double distilled water to remove the excess oil red 0 and then examined using an inverted phase contrast Olympus microscope.

(5) Investigation of the Antioxidant Effect of TADN

3T3-L1 cells and Raw 264.7 cells were induced by the above-mentioned method and lipopolysaccharide (LPS), respectively. During the induction process, the two types of cells were subjected to antioxidation treatment with TADN or NTADN, and then stained with 5 μM of $H_2DCFDA$ and Hoechst 33342 to evaluate the intracellular ROS level.

Results of the above investigations were analyzed as follows.

(1) Antiobesity Effect of TADN In Vitro

Figure 11:
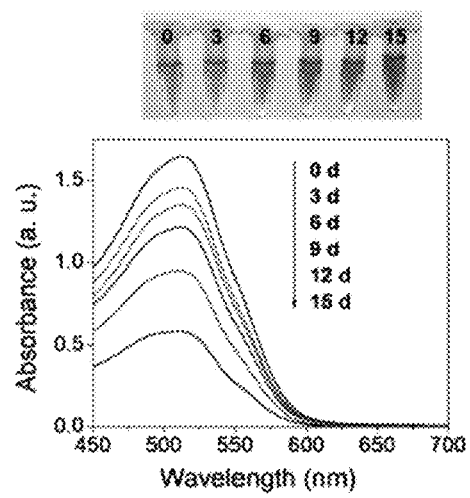
FIG. 11 shows a UV-Vis determination of droplet accumulation in 3T3-L1 cells.
Figure 12:
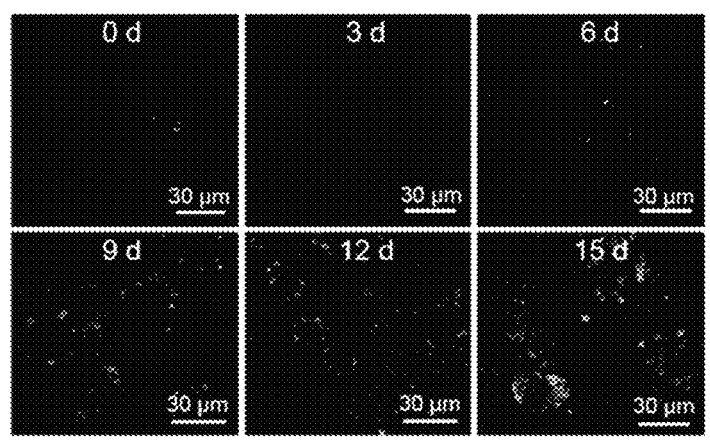
FIG. 12 shows confocal imaging of 3T3-L1 cells stained with $H_2DCFDA$.

The investigations on the antioxidant and anti-inflammatory activities of TADN were conducted as follows. The results were shown in FIG. 11, obvious accumulation of lipid droplets was observed, indicating gradual differentiation of 3T3-L1 cells. Meanwhile, the differentiation of preadipocytes exhibited a significant time-dependent increase in the intracellular free radical level (FIG. 12). Since the cells displayed obvious differentiation characteristic after 9 days of the induction, the cells were collected at the $9^{th}$ day of the induction for subsequent experiments.

Figure 13:
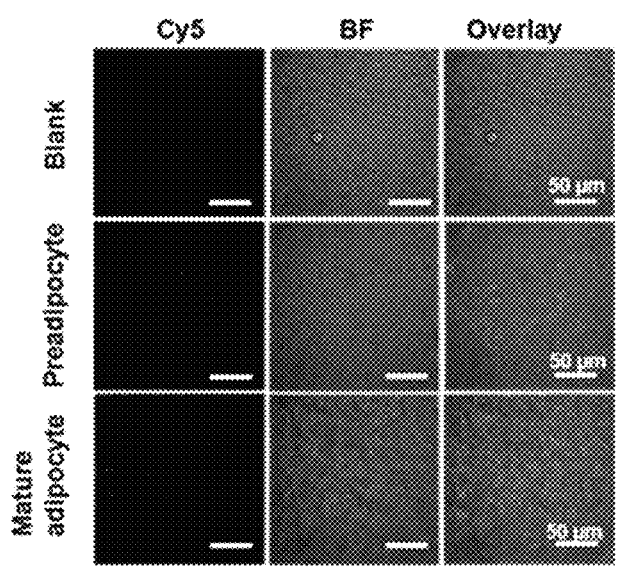
FIG. 13 illustrates the confocal imaging of Cy5-TADN specifically binding with mature 3T3-L1 adipocytes.
Figure 14:
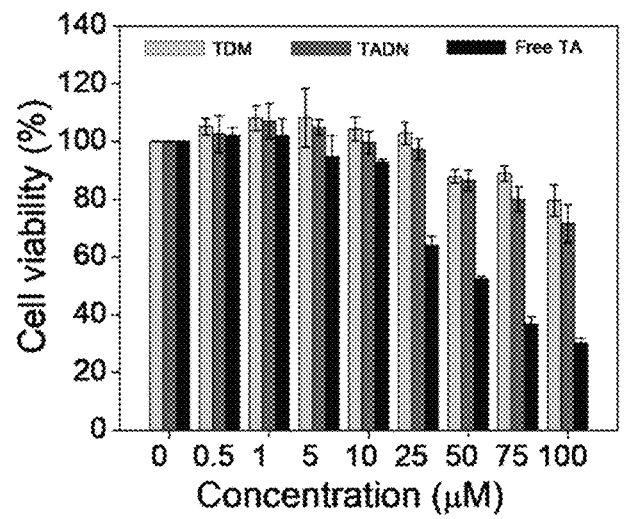
FIG. 14 shows the cytotoxicity of TDM, TADN and TA on 3T3-L1 cells.
Figure 15:
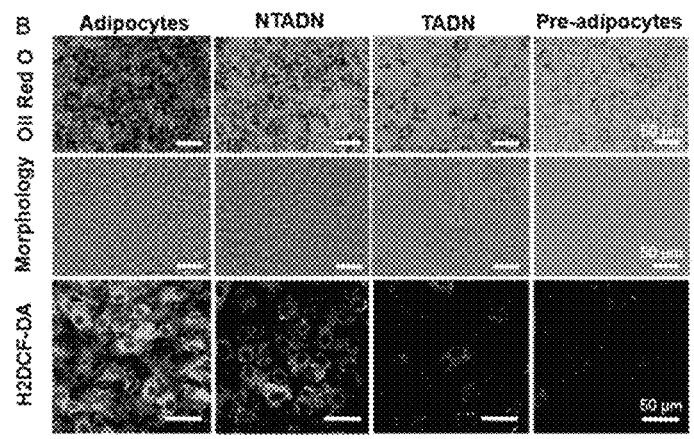
FIG. 15 illustrates the oil red 0 staining and confocal imaging of pre-adipocytes and mature adipocytes treated with TADN or NTADN.

The investigation on the antiobesity activity of TADN was carried out as follows. Specifically, Cy5-dUTP was integrated to TADN or NTADN through RCR to form Cy5-TADN or Cy5-NTADN, which was employed to explore the adipocyte-targeting ability of TADN. As shown in FIG. 13, compared to the mature adipocytes treated with Cy5-NTADN, the mature adipocytes treated with Cy5-TADN presented significantly enhanced red fluorescence, indicating excellent targetability and internalization ability of TADN. In addition, the cytotoxicity test results showed increasing cytotoxicity at a concentration of TA above 25 μM, while neither TDM nor TADN presented obvious effects on the cell proliferation and differentiation even at a concentration above 100 μM (FIG. 14). On the basis of the results, TADN was further studied for its antiobesity effect. In order to evaluate the antiobesity intervention effect of TADN on 3T3-L1 cells, the cells were subjected to TADN or NTADN intervention once every three days during the induction for a total of three times. The ROS level and the accumulation of lipid droplets in the cells were characterized by $H_2DCFDA$ fluorescence imaging and oil red 0 staining, respectively. Obviously, compared to the cells treated with NTADN, TADN could significantly mitigate the accumulation of both ROS and lipid droplets, evidenced by the slight Oil Red 0 staining and weak $H_2DCFDA$ fluorescence intensity, indicating higher antioxidant and antiobesity activities of TADN (FIG. 15). The above results demonstrated that TADN had considerable potential in in vitro antiobesity therapy.

(2) Suppressing Immune Cell Activation of TADN

Figure 16:
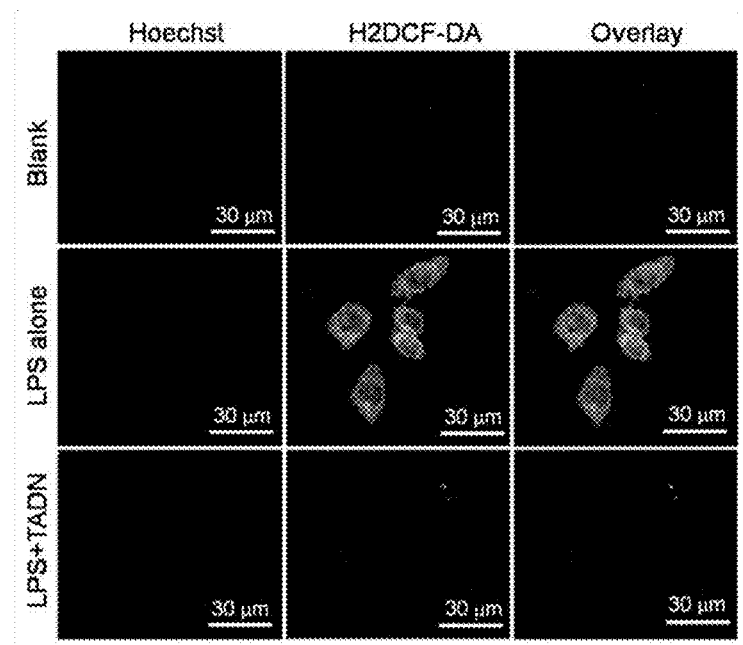
FIG. 16 shows the $H_2DCFDA$ confocal imaging of Raw 264.7 cells treated with TADN and LPS.

During the differentiation into adipocytes, a disorganized intracellular redox and inflammatory microenvironment will quickly activate and recruit the surrounding immune cells and inflammatory cells to produce more reactive oxygen species, reactive nitrogen species and inflammatory factors, which will cascade a series of diseases, including systemic inflammation and insulin resistance. Since macrophages are the main monocytes and infiltrating inflammatory cells during the induction of obesity, Raw 264.7 cells stimulated by LPS were used as an inflammatory cell model to evaluate the antioxidant effect of TADN. As shown in FIG. 16, confocal imaging clearly revealed a dramatically enhanced fluorescence in the cells in response to LPS stimulation compared to control cells, indicating the generation of excessive free radicals. In contrast, significantly decreased fluorescence intensity in the Raw 264.7 cells treated with TADN and LPS indicated effective elimination of intracellular free radicals. TADN could be used as an effective antioxidant in suppressing the activation of immune cells (FIG. 16).

Example 3 Animal Experiments

In-Vivo Test (1) In-Vivo Test and Establishment of Obesity Model

Male C57BL/6J mice were purchased from Hunan SJA Laboratory Animal Co., Ltd, and the animal experiment was approved by the Laboratory Animal Management Center of Hunan University. To build the obesity model, the mice, aged 6 weeks, were fed with a high fat diet (HFD, 60% calories, penSourceDiet D12492, Research Diet). The mice were weighed once a week until they reached a weight of about 30 g.

(2) Biodistribution of TADN

After the mice were fed a high fat diet to about 30 g, the normal mice and the obese mice were intravenously administered with Cy7-TADN or Cy7-NTADN through the tail vein. At 24 h post-injection, mice were imaged using an in vivo imaging system (IVIS) Lumina II (Caliper Life Science, USA) at different time points. Mice were then sacrificed, and the main organs (heart, liver, spleen, lung and kidney) were collected and imaged.

(3) In-Vivo Antiobesity Activity of TADN

The in-vivo antiobesity effect of TADN was investigated as follows. Obese mice were randomly divided into 4 groups, 8 in each. Specifically, the four groups were (i) HFD mice+PBS; (ii) HFD mice+TADN; (iii) HFD mice+NTADN; and (iv) HFD mice+TA, respectively. A group of mice fed a normal diet was used as the control group. The mice in each treatment group were treated twice a week until the $9^{th}$ week, and their weight was recorded once a week. The mice were sacrificed at the $10^{th}$ week, and the liver tissues were isolated, weighed and then subjected to immunohistochemical staining for subsequent pathological analysis.

(4) Test of Systemic Toxicity

To investigate the systemic toxicity of TADN, normal C57BL/6 mice were treated with PBS, TADN or NTADN through the tail vein. At 24 h post-injection, their organs, including the heart, liver, spleen, lung, and kidney, were isolated, immersed with formalin and stained with hematoxylin-eosin (H&E) for subsequent pathological analysis.

The results were analyzed as follows.

(1) In vivo biodistribution of TADN

Figure 17A:
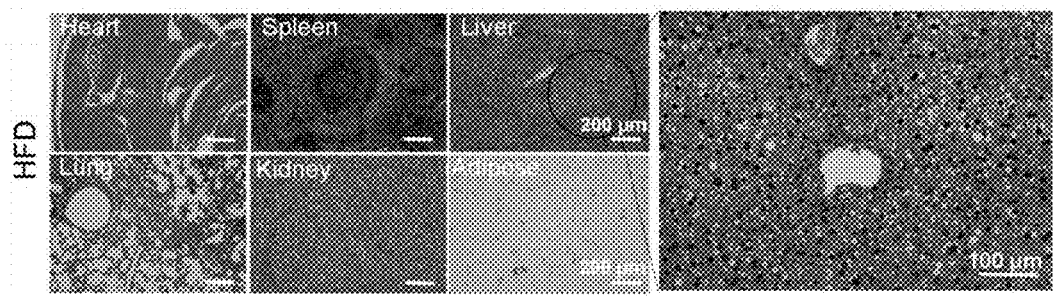
FIGS. 17A-B depict the H&E staining results of main organs of mice fed with HFD (A) and ND (normal diet) (B).
Figure 17B:
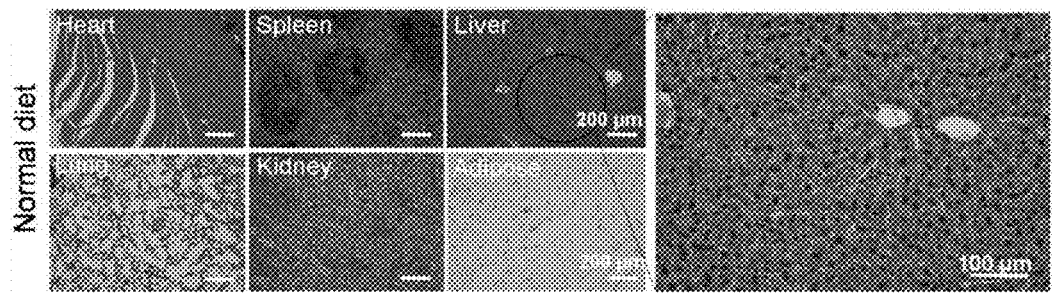
Figure 18:
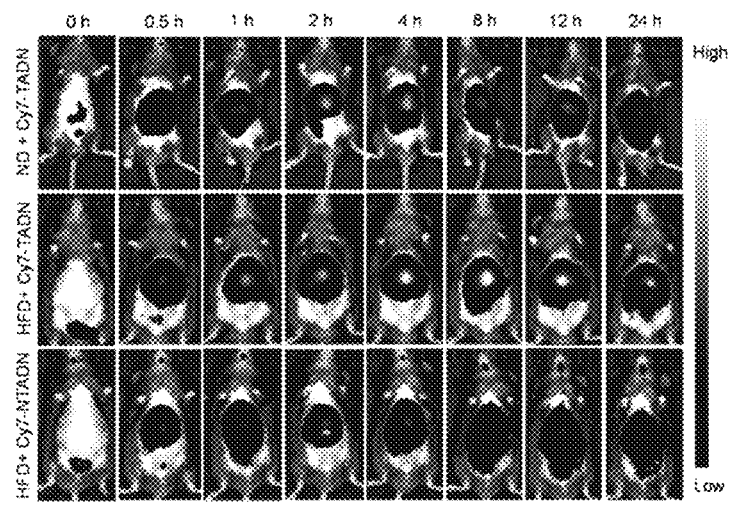
FIG. 18 shows in vivo fluorescence imaging of normal mice and HFD mice at different time points after tail intravenous injection of Cy7-TADN or Cy7-NATDN.
Figure 19:
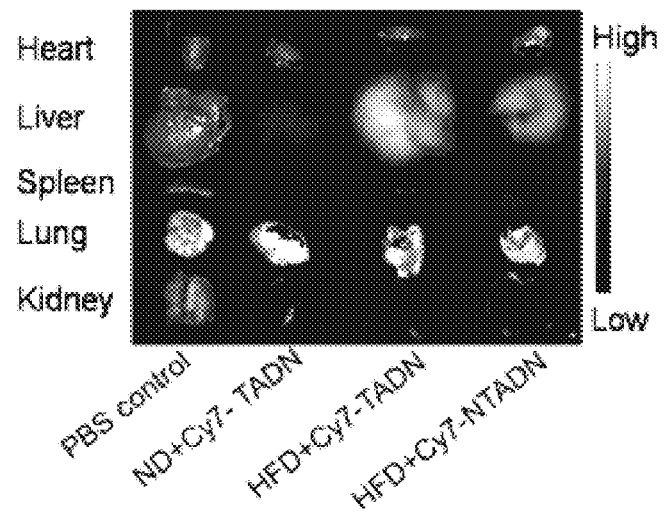
FIG. 19 shows fluorescence imaging of major organs (heart, liver, spleen, lung and kidney) of normal mice and HFD mice after tail intravenous injection of Cy7-TADN or Cy7-NATDN.
Figure 20:
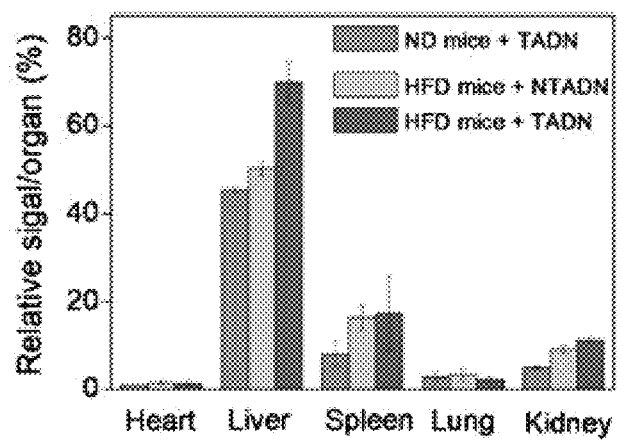
FIG. 20 illustrates the relative quantification of the fluorescence imaging results presented in FIG. 19.

On the basis of wide in vitro antioxidant activity and excellent antiobesity effect, TADN was further investigated for its in vivo antiobesity activity using the obesity mouse model induced by a high fat diet. After being fed with a high fat diet for several weeks, the mice suffered obvious steatosis and accumulation of lipid droplets in the liver tissue, which confirmed that the obesity mouse model was successfully constructed (FIGS. 17A-B). To verify the adipocyte-targeting ability of TADN in vivo, Cy7-labeled TADN and NTADN were intravenously administered to HFD-fed mice or normal diet-fed mice through the tail vein. As shown in FIGS. 18-20, both nanostructures showed time-dependent accumulation in the liver of obese mice in comparison to other organs, but enhanced fluorescence intensity of Cy7 in TADN-treated HFD mice demonstrated the efficient targeting capability of the adipocyte-targeting DNA nanodrugs. Moreover, the accumulation level of TADN in the liver with steatosis of the HFD mice was superior to that in the liver of the ND mice. Since the liver played an important role in the nutrient intake and energy metabolism, it was prone to inflammation and rapidly developed into steatosis under continuous HFD stimulation. Therefore, under the systemic administration, it was understandable that the adipocyte-targeting TADN underwent obvious accumulation in the liver compared to other organs.

(2) In Vivo Antiobesity Activity of TADN

Figure 21:
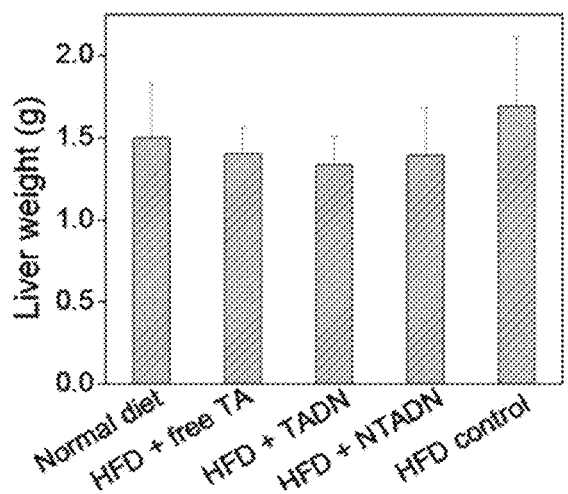
FIG. 21 shows liver weight of ND and HFD mice after being treated with TADN, NTADN or TA.
Figure 22:
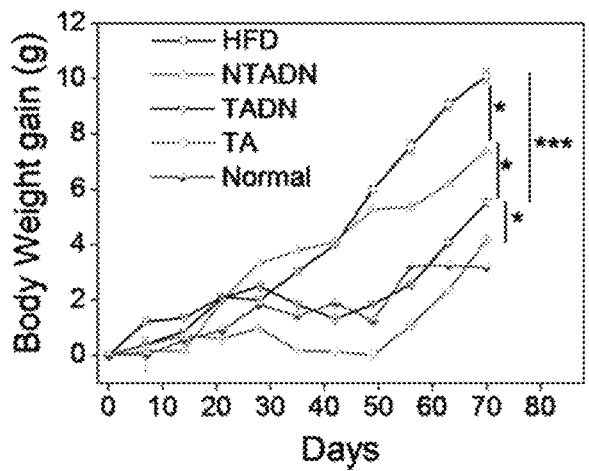
FIG. 22 shows body weight gain of ND and HFD mice treated with TADN, NTADN or TA.
Figure 23:
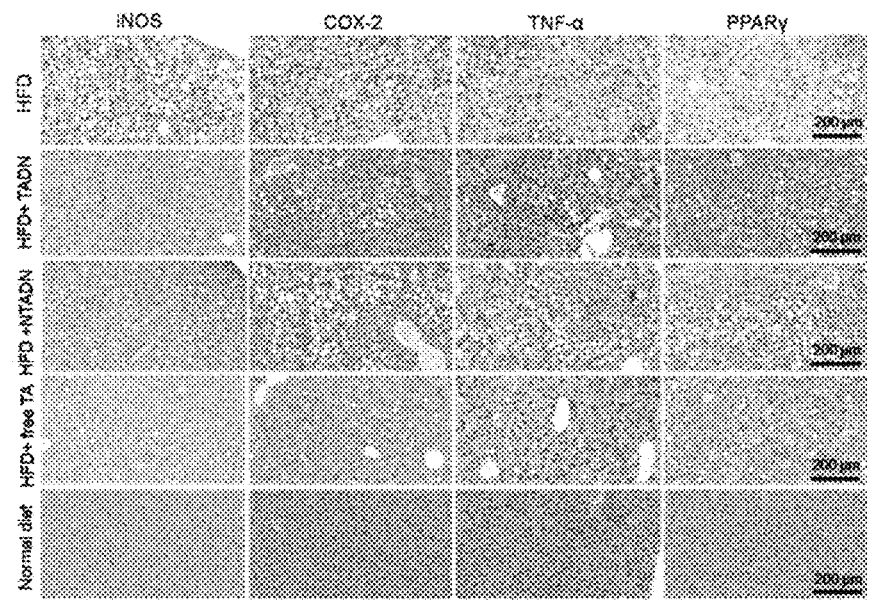
FIG. 23 illustrates immunohistochemical staining of liver tissue of ND or HFD mice after being treated with TADN, NTADN or TA.

On the basis of in vivo targetability towards liver, TADN was further investigated to determine whether its systemic administration can effectively prevent hepatic steatosis and weight gain in the HFD-induced obesity mouse model. Specifically, the HFD-induced C57BL/6 obese mice were randomly divided into four experimental groups, and normal diet-fed C57BL/6 mice were used as the control. The obese mice were intravenously injected with TADN, NTADN or TA twice a week at a dose of 5 mg TA/kg, and ND-fed control mice were injected with PBS. Mice were weighed once a week. After 10 weeks, mice were scarified, weighed, and livers were harvested for histopathologic analysis. The results showed that compared to other groups, the mice treated with TADN were effectively controlled in the liver weight and body weight (FIGS. 21-22). The expression of various inflammatory cytokines or other regulatory factors (induced nitric oxide synthase (iNOS), cyclooxygenase-2 (COX-2), peroxisome (PPAR) γ and tumor necrosis factor α (TNF-α)) was further analyzed by immunohistochemical analysis (IHC) (FIG. 23). Consistent with the above results, the TADN can effectively inhibit the expression of these inflammatory factors and was thus considered to be an effective nanodrug for the alleviation of inflammation and liver damage.

(3) Test Results of Systemic Toxicity

Figure 24:
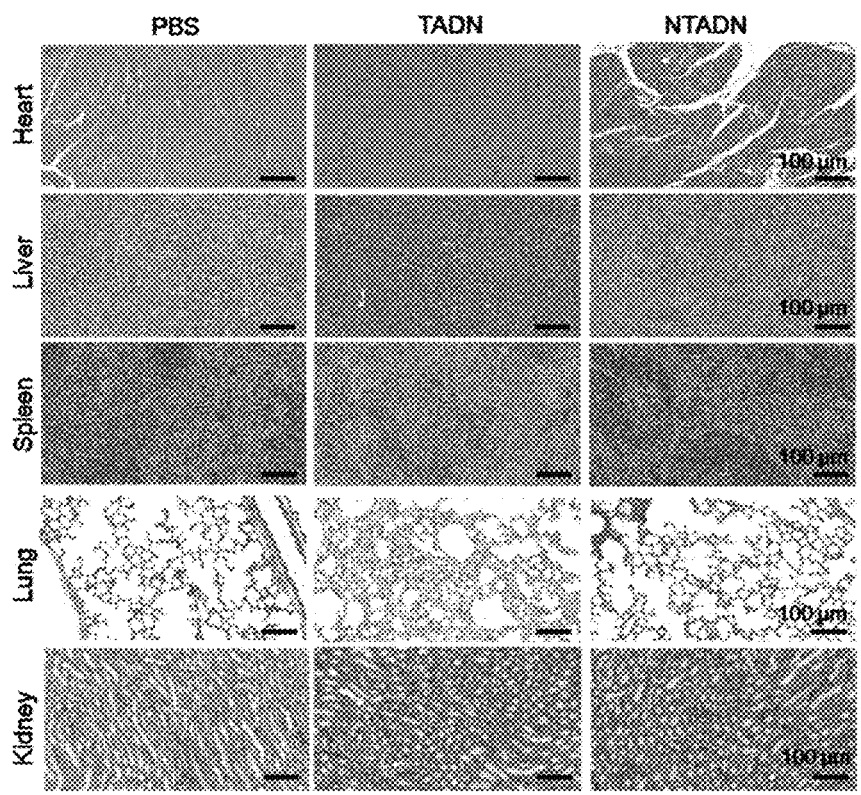
FIG. 24 shows H&E staining results of main organs of healthy C57BL/6 mice after treated with TADN or NTADN.

The safety of the antiobesity drugs must be high enough to be approved by the FDA, and in view of this, the potential adverse effects of TADN were evaluated herein. The normal C57BL/6 mice were injected with a therapeutic dose of PBS, NTADN and TADN, respectively, and the main organs were collected for histological examination after 24 h. The H&E staining results were illustrated in FIG. 24, from which it can be found that the treated mice had no obvious tissue damage in their main organs, indicating the good biocompatibility of the TADN nanodrug.

What is claimed is:

1. An adipocyte-targeting DNA nanodrug, comprising:
an adipocyte-targeting DNA microstructure; and
tannic acid;
wherein the tannic acid is loaded into the adipocyte-targeting DNA microstructure through multiple hydrogen bonds to fabricate the adipocyte-targeting DNA nanodrug; and a weight ratio of the adipocyte-targeting DNA microstructure to the tannic acid is 1:25-30; and
wherein the adipocyte-targeting DNA microstructure comprises a phosphorylated DNA template of SEQ ID NO: 1 and a primer of SEQ ID NO: 2.

2. The adipocyte-targeting DNA nanodrug of claim 1, wherein the adipocyte-targeting DNA microstructure is a spherical particle with a densely layered structure with an average size of 1-2 μm.

3. The adipocyte-targeting DNA nanodrug of claim 2, wherein the adipocyte-targeting DNA microstructure is formed from a DNA sequence as shown in SEQ ID NO: 1 through rolling circle replication (RCR) and dense packaging-driven DNA self-assembly processes.

4. The adipocyte-targeting DNA nanodrug of claim 3, wherein the adipocyte-targeting DNA microstructure is prepared through steps of:
(1) mixing the phosphorylated DNA template (SEQ ID NO: 1) carrying an adipocyte-targeting aptamer sequence and the primer (SEQ ID NO: 2) in a DNA ligase buffer; annealing the reaction mixture; and subjecting the annealed product to ligation in the presence of E. coli DNA ligase to form a circularized DNA template; and
(2) subjecting the circularized DNA template to polymerization in a polymerase buffer containing BSA in the presence of phi29 DNA polymerase and dNTP; heating the reaction mixture to terminate the polymerization; and washing the reaction mixture to obtain the adipocyte-targeting DNA microstructure.

5. The adipocyte-targeting DNA nanodrug of claim 4, wherein in step (1), a concentration of the phosphorylated DNA template is 8-12 μM; a concentration of the primer is 8-12 μM; the DNA ligase buffer contains 5 mM of Tris-HCl, 1 mM of $MgCl_2$, 0.1 mM of ATP and 1 mM of dithiothreitol; a concentration of the E. coli DNA ligase is 50-70 U/μL; a volume ratio of the phosphorylated DNA template to the primer to the DNA ligase buffer to the E. coli DNA ligase is (2-4):(5-7):(30-60):(7-9); the annealing is programmed as follows: 95° C. for 5 min and cooling to room temperature within 2 h; and the ligation is performed at 16° C. for 3 h.

6. The adipocyte-targeting DNA nanodrug of claim 4, wherein in step (2), a concentration of the circularized DNA template is 0.5-0.7 μM; a concentration of the phi29 DNA polymerase is 8-12 U/μL; a content of bovine serum albumin (BSA) is 0.04%-0.06%; the polymerase buffer contains 50 mM of Tris-HCl, 10 mM of $(NH_4)_2SO_4$, 10 mM of $MgCl_2$ and 4 mM of dithiothreitol in a volume ratio of (45-55):(15-25):(0.5-1.5):(95-105); the polymerization is performed at 28-32° C. for 18-30 h; and the heating is performed at 70-80° C. for 8-12 min.

7. A method of preparing the adipocyte-targeting DNA nanodrug of claim 1, comprising:
adding a tannic acid solution to a solution of the adipocyte-targeting DNA microstructure; reacting the reaction mixture at a preset temperature under shaking; followed by centrifugation to collect the adipocyte-targeting DNA nanodrug.

8. The method of claim 7, wherein a concentration of the solution of the adipocyte-targeting DNA microstructure is 0.2-0.4 μM; a concentration of the tannic acid solution is 5-15 mM; and a volume ratio of the solution of the adipocyte-targeting DNA microstructure to the tannic acid solution is (0.5-1.5): (0.5-1.5).

9. A method of treating obesity in a subject in need thereof, comprising:
administering a therapeutically effective amount of the adipocyte-targeting DNA nanodrug of claim 1 to the subject.

* * * * *

SEQUENCE LISTING

<160> NUMBER OF SEQ ID NOS: 4

<210> SEQ ID NO 1
<211> LENGTH: 99
<212> TYPE: DNA
<213> ORGANISM: Artificial Sequence
<220> FEATURE:
<223> OTHER INFORMATION: synthetic

<400> SEQUENCE: 1
atcgacctct gggttatgcc tgcagtgtgt gtgatgcctg ttatttggcc tgccggtggg    60
cccagcacgc ttccgcgcgt accaacaatt gttggtacg                          99

<210> SEQ ID NO 2
<211> LENGTH: 36
<212> TYPE: DNA
<213> ORGANISM: Artificial Sequence
<220> FEATURE:
<223> OTHER INFORMATION: synthetic

<400> SEQUENCE: 2
cataacccag aggtcgatcg taccaacaat tgttgg                             36

<210> SEQ ID NO 3
<211> LENGTH: 40
<212> TYPE: DNA
<213> ORGANISM: Artificial Sequence
<220> FEATURE:
<223> OTHER INFORMATION: synthetic

<400> SEQUENCE: 3

```
caccggcagg ccaaataaca ggcatcacac acactgcagg                          40

<210> SEQ ID NO 4
<211> LENGTH: 99
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (19)..(58)
<223> OTHER INFORMATION: n is a, c, g, or t

<400> SEQUENCE: 4
atcgacctct gggttatgnn nnnnnnnnnn nnnnnnnnnn nnnnnnnnnn nnnnnnnngg   60
cccagcacgc ttccgcgcgt accaacaatt gttggtacg                          99
```